United States Patent [19]
Lu

[11] Patent Number: 5,318,523
[45] Date of Patent: Jun. 7, 1994

[54] DRUG-FEEDER FOR CHILDREN

[76] Inventor: Jieh-Shan Lu, No. 23, Lane 783, Wen Hwa Road, Nan Tou City, Nan Tou Hsien, Taiwan

[21] Appl. No.: 90,309

[22] Filed: Jul. 13, 1993

[51] Int. Cl.$^5$ ............................................. A61J 7/00
[52] U.S. Cl. ........................................ 604/77; 604/54
[58] Field of Search ............... 604/77, 78, 79, 54, 604/212, 213

[56] References Cited

U.S. PATENT DOCUMENTS

| | | | |
|---|---|---|---|
| 3,572,337 | 3/1971 | Schunk | 604/77 |
| 4,405,321 | 9/1983 | Budoff | 604/212 |
| 4,519,794 | 5/1985 | Sneider | 604/212 |
| 4,880,409 | 11/1989 | Winblad et al. | 604/77 |
| 4,966,312 | 10/1990 | Waring | 604/77 |
| 5,222,940 | 6/1993 | Wilk | 604/77 |
| 5,236,415 | 8/1993 | Stallings | 604/77 |

Primary Examiner—Paul J. Hirsch
Attorney, Agent, or Firm—Bacon & Thomas

[57] ABSTRACT

A drug-feeder for children comprises a drug chamber and a drug guider. A rotating member is disposed at a front end of the drug guider and can be rotarily adjusted to optionally inject the liquid drug in the drug chamber in an upward direction or two lateral directions to cure different areas in the oral cavity of the child. The drug chamber and the drug guider are inclinedly connected to form an angle about 130 degrees between them so that when the drug-feeder is Placed in the mouth of the child, the oral cavity of the child can still be clearly seen and no drug will drop onto the tongue of the child before the drug guider reaches the desired position for treatment, preventing the child from resisting against the drug feeding due to the bad taste of drug.

3 Claims, 5 Drawing Sheets

DRUG-FEEDER FOR CHILDREN

BACKGROUND OF THE INVENTION

The present invention relates to a drug-feeder for children. The front end of the drug-feeder is disposed with a rotating member which is rotarily adjustable for optionally injecting the drug in an upward direction and or two lateral directions to cure the different areas in the oral cavity of a child so as to achieve the best curing effect. The drug-feeder has a drug guider and a drug chamber downward inclinedly connected to the drug guider to include an angle about 130 degree between them so that when the drug-feeder is Placed in the mouth of the child, the oral cavity of the child can be still clearly seen to facilitate the feeding of drug.

When a child is sick and needs medical treatment, an oral liquid medicine is currently most widely used one. With respect to a child, it is often difficult to accomplish the drug feeding. Therefore, a drug-feeder for a child has been developed for eliminating the trouble caused during feeding the child an oral liquid drug with a spoon. Although such conventional drug-feeder can eliminate the shortcoming that the child will resist the drug feeding due to the taste of the drug, the conventional drug-feeder still cannot completely avoid the drops of drug from incidentally dropping onto the tongue of the child. Moreover, to avoid the child from being choked by the drug, the child is often properly laid inclinedly when being fed with the conventional drug-feeder properly downward inclinedly positioned above the tongue of the child. At this point, the drug in the feeder will usually gradually drop out of the drug-feeder as shown in FIG. 7. As a result, the child will more or less taste the drug and resist the drug feeding. In addition, when the conventional drug-feeder is placed in the mouth of the child, the sight of the oral cavity of the child is obstacled by the drug-feeder and the areas needing cure cannot be clearly seen and thus the curing effect is inversely affected.

SUMMARY OF THE INVENTION

It is therefore a primary object of the present invention to provide a drug-feeder for children which can effectively eliminate the shortcoming of the conventional drug-feeder and prevent the drug in the drug-feeder from gradually and undesirably dropping onto the tongue of the child before the drug-feeder reaches the areas needing cure when it is in an inclined position in the mouth of the child; in addition, the drug guider and the drug chamber of the drug-feeder are properly downward inclinedly connected, permitting the oral cavity of the child to be clearly seen even when the drug-feeder is Placed in the mouth so as to facilitate the drug feeding.

It is a further object of the Present invention to provide the above drug-feeder Provided with a rotating member which can be rotarily adjusted to optionally inject the drug upward or laterally for achieving the best curing effect on different areas of the oral cavity of the child.

The structure, features, and other objects of the present invention and the technical means adopted by the present invention to achieve the objects thereof can be best understood through the following description of the preferred embodiments and the accompanying drawings, wherein:

DETAILED DESCRIPTION OF THE PREFERRED EMBODIMENTS

Figure 1:
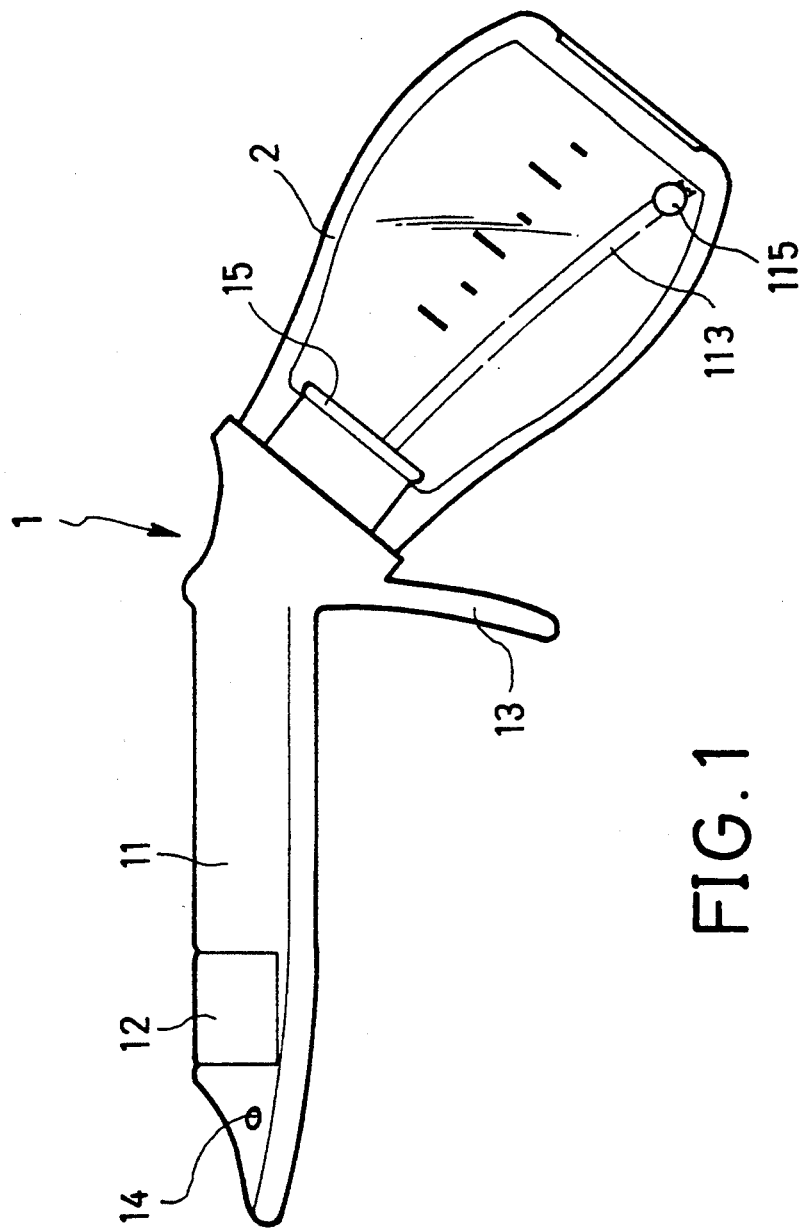
FIG. 1 is a side view of the Present invention showing the general layout thereof.

Please refer to FIG. 1. The drug-feeder 1 of the present invention is mainly composed of a drug chamber 2 for containing a liquid drug 3 therein and a drug guider 11 connected to the front of the drug chamber 2. A front end of the drug guider 11 is disposed with a rotating member 12. The rotation of the rotating member 12 Permits the drug-feeder 1 to optionally upward inject the drug in a single direction or horizontally inject the drug in two lateral directions.

Figure 2:
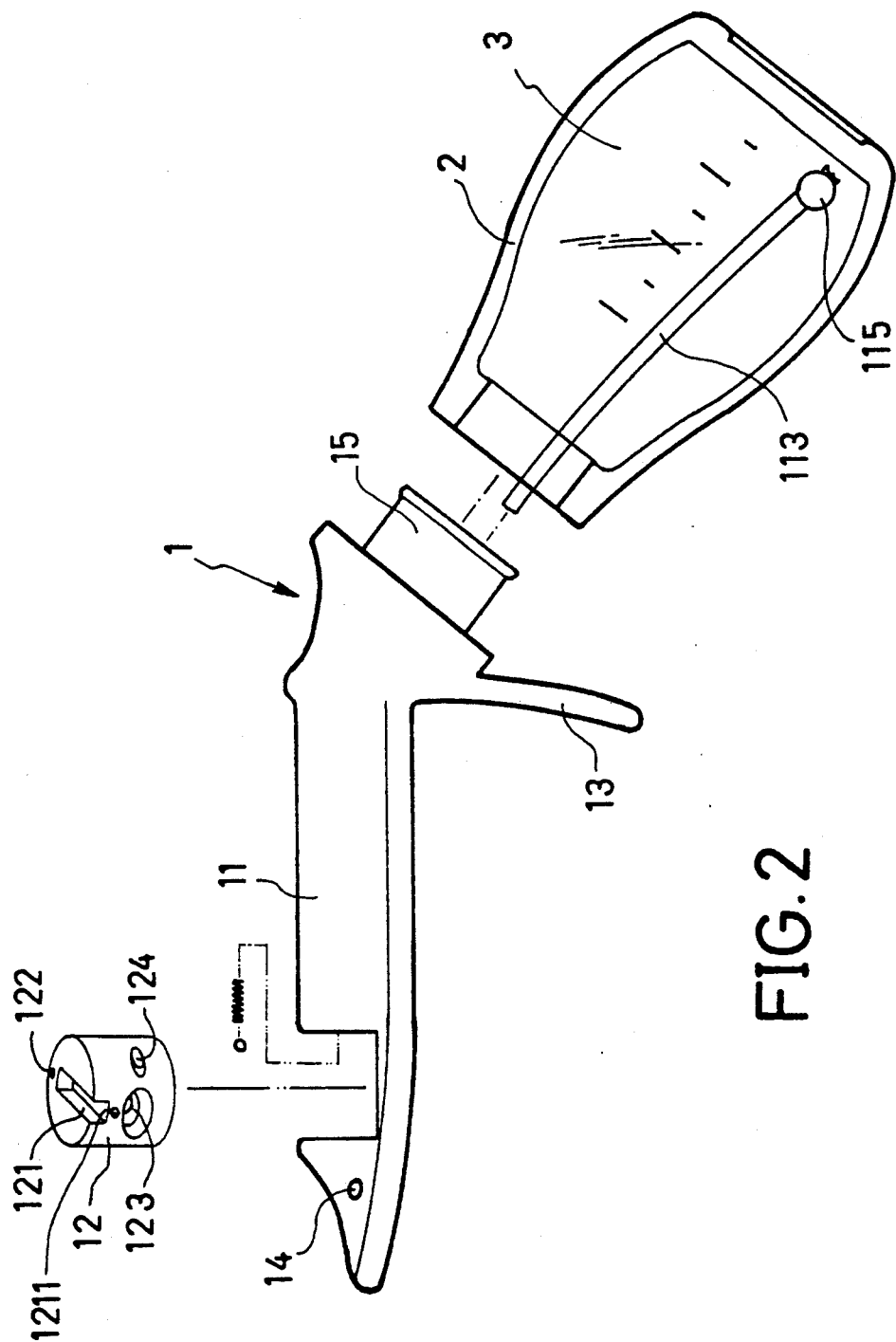
FIG. 2 is an exploded view according to FIG. 1.
Figure 3A:
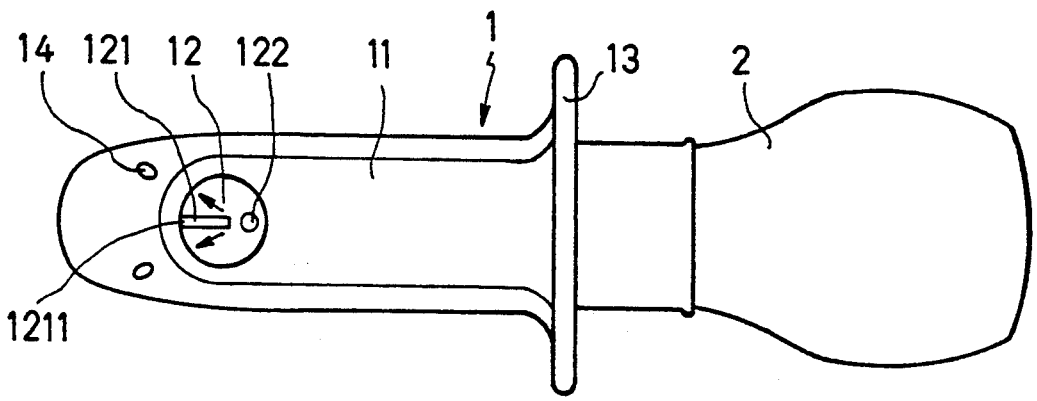
FIG. 3 includes a top view and a longitudinally sectional view of the present invention.
Figure 3B:
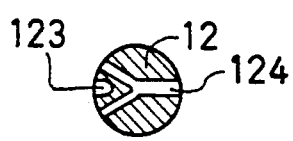
Figure 3C:
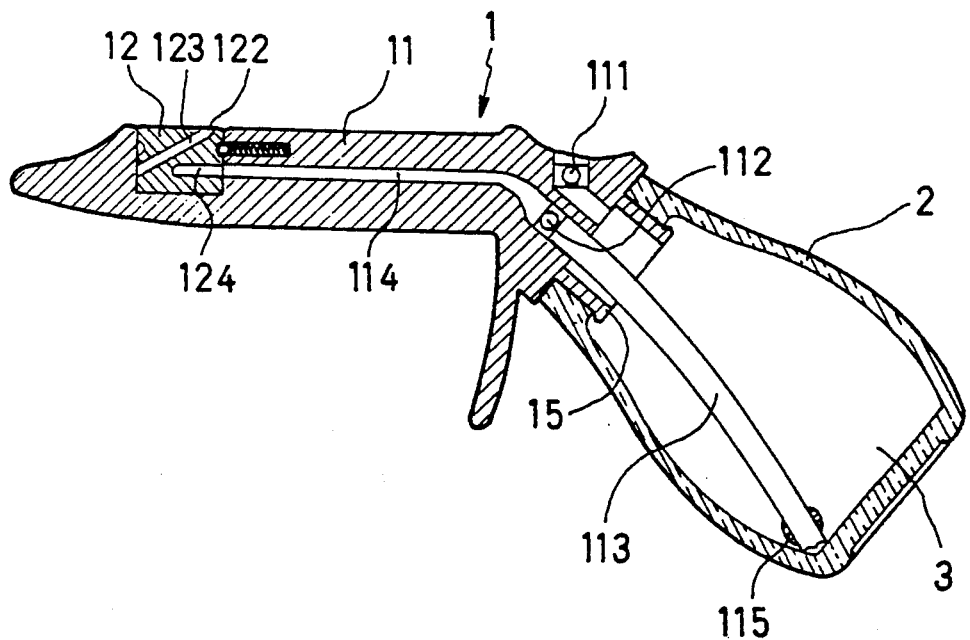
Figure 6:
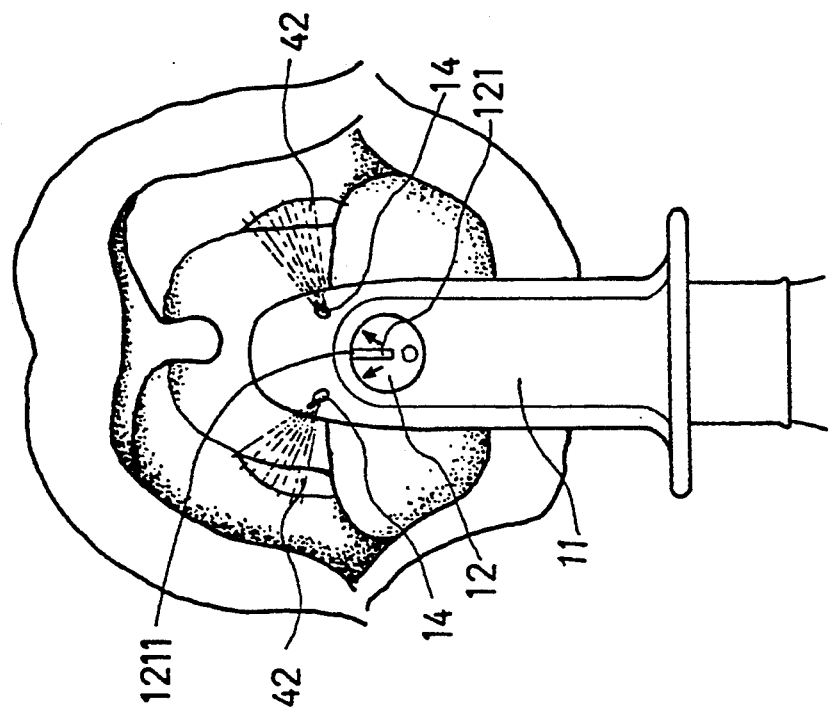
FIG. 6 shows that the liquid drug in the drug-feeder of the present invention is injected laterally in two directions.
Figure 5A:
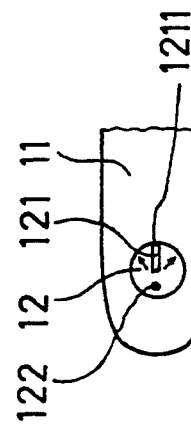
FIG. 5 shows that the liquid drug in the drug-feeder of the present invention is injected upward in one single direction.
Figure 5B:
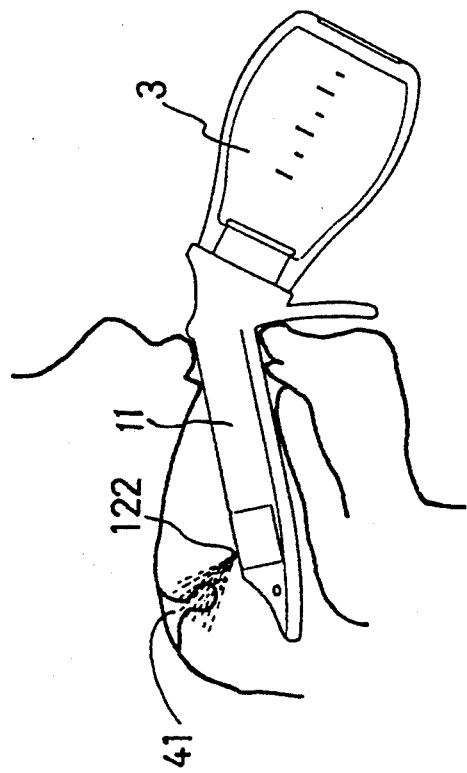
Figure 4:
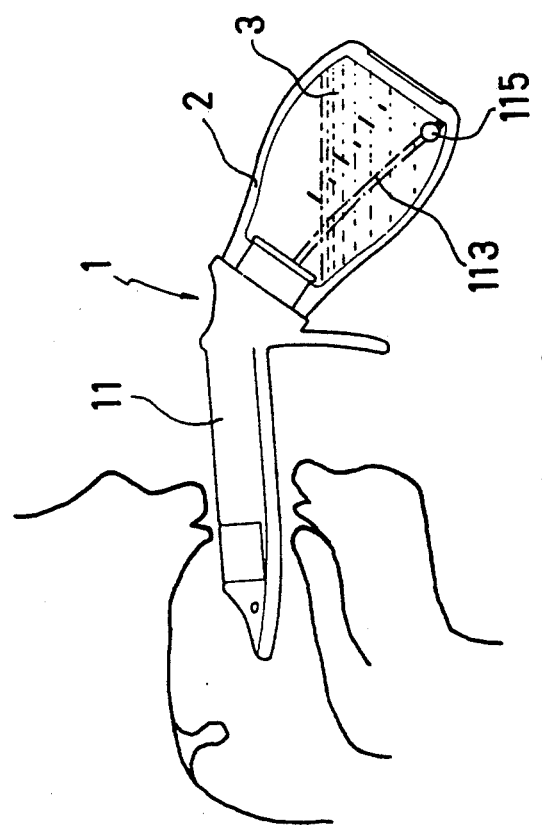
FIG. 4 shows the application of the Present invention.

Please now refer to FIGS. 2 and 3. The drug guider 11 is substantially a long and flat tube having an elliptical cross-section. The rotating member 12 is formed with an upward inclined tunnel 123, a Y-shaped tunnel 124, and an upper adjusting recess 121, whereby when an end opening 1211 of the recess 121 formed on the outer Periphery of the rotating member 12 is adjusted toward the front end of the drug-feeder 1, the Y-shaped tunnel 124 becomes communicable with an inner guide tube 113 in the drug chamber 2, permitting the liquid drug 3 therein to be transferred through a flow passage 114 of the drug guider 11 and the Y-shaped tunnel 124 and then injected outward from two horizontal injecting orifices 14 formed on two sides of the front end of the drug guider 11, while when the opening 1211 of the recess 121 is adjusted reversely, the upward inclined tunnel 123 becomes communicable with the flow passage 114 so that the liquid drug 3 is transferred through the flow passage 114 and the tunnel 123 and then injected outward from an upper injecting orifice 122 at one end of the upward inclined tunnel 123. Accordingly, the liquid drug 3 can be optionally injected toward different areas in the oral cavity to achieve optimal medical treatment effects.

An arcuate stopper 13 is integrally formed under the drug guider 11, whereby when the drug guider 11 is extended into the mouth of a child for feeding the drug, the arcuate stopper 13 can abut against the lower lip and chin of the child and Prevents the drug guider 11 from excessively extending into the mouth and thus injuring the throat of the child. A coupling Portion 15 is integrally formed behind the arcuate stopper 13 to downward incline therefrom such that there is an angle about 130 degrees formed between the drug guider 11 and the coupling portion 15 and to couple with the drug chamber 2. A first and a second check valves 111, 112 are disposed in the coupling portion 15, wherein the first check valve 111 permits the air to irreversibly enter the drug chamber 2, while the second check valve 112

Permits the liquid drug 3 to irreversibly flow through the guide tube 113 and the flow passage 114. A weight member 115 is disposed at a lower end of the guide tube 113 opposite to the second check valve 112, permitting all the liquid drug 3 in the drug chamber 2 to be transferred outward through the guide tube 113 and the flow passage 114 to the tunnel 123 or 124. The drug chamber 2 can be made of transparent silicone resin or rubber and marked with scales for accurately dispensing the drug.

Figure 7:
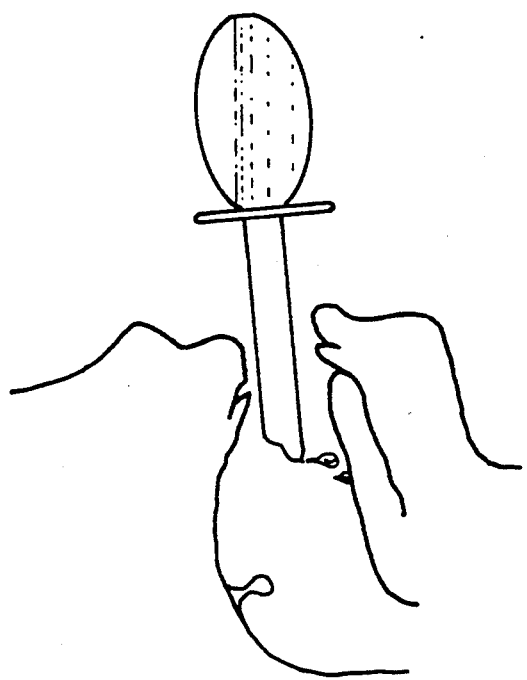
FIG. 7 shows the application of a conventional drug-feeder.

According to the above arrangement, when the drug-feeder of the present invention is Placed into the mouth of a child, no liquid drug 3 will undesirably drop onto the tongue of the child to make the child taste the drug before the drug guider 11 reaches the the normal feeding position and thus resists the drug feeding as shown in FIG. 7. Moreover, the drug can be optionally injected upward or laterally to oure the uvula 41 or tonsil 42, respectively, for achieving the best curing effect.

It is to be understood that the form of the present invention shown and disclosed is to be taken as a preferred embodiment of the Present invention and that various changes in the shape, size and arrangement of parts may be resorted to without departing from the spirit of the present invention or the scope of the subjoined claims.

What is claimed is:

1. A drug-feeder for children, comprising:
   a long and flat tube-like drug guider having a substantially elliptical cross section, said drug guider having a front end Portion which is formed with two horizontal injecting orifices and a recess, a flow passage formed inside said drug guider, an arcuate stopper being integrally formed under a rear end of said drug guider for abutting against the lower lip and chin of a child using said drug-feeder, and a downward inclinedly extended coupling portion formed behind said arcuate stopper and forming an angle about 130 degrees between said coupling portion and said drug guider;
   a rotating member rotatably disposed in said recess of said drug guider having a top adjusting recess, an upward inclined tunnel, and a Y-shaped tunnel; said upward inclined tunnel having an upper injecting orifice, and said Y-shaped tunnel being communicable with said two horizontal injecting orifices formed on said drug guider; and
   a drug chamber made of transparent silicone resin or rubber with marked scales thereon for accurate dispensing of drug having a guide tube disposed therein to communicate with said flow passage of said drug guider and being detachably connected to said drug guider via said downward inclindedly extended coupling Portion of said drug guider, such that the areas needing cure in the oral cavity of a child can be clearly seen even when said drug-feeder is placed in the mouth of the child, and that no liquid drug in said drug chamber will drop onto the tongue of the child before said drug guider reaches the areas needing cure, causing the child to taste the drug and thus resists the drug feeding.

2. A drug-feeder as claimed in claim 1, wherein a first and a second check valves are disposed in said coupling portion of said drug guider, said first check valve permitting the air to irreversibly enter said drug chamber while said second check valve permitting the liquid drug to irreversibly flow outward from said drug chamber through said guide tube to said flow Passage of said drug guider and finally to the oral cavity of the child.

3. A drug-feeder as claimed in claim 1, wherein said adjusting recess has an opening end formed at an outer periphery of said rotating member such that when said opening of said adjusting recess is turned to point a front end of said drug-feeder, said Y-shaped tunnel is communicable with said guide tube in said drug chamber through said flow Passage of said drug guider, permitting said liquid drug to be transferred from said drug chamber through said flow Passage of said drug guider to said Y-shaped tunnel and then injected outward from said two horizontal injecting orifices on said front end portion of said drug guider, while when said opening of said adjusting recess is turned to Point backward, said upward inclined tunnel is communicable with said flow passage so that said liquid drug is transferred through said flow passage to said upward inclined tunnel and then injected outward from said upper injecting orifice thereof.

* * * * *